US007627362B2

United States Patent
Gregory et al.

(10) Patent No.: US 7,627,362 B2
(45) Date of Patent: *Dec. 1, 2009

(54) METHOD AND APPARATUS FOR PRODUCING AN ELECTRICAL PROPERTY IMAGE OF SUBSTANTIALLY HOMOGENEOUS OBJECTS CONTAINING INHOMOGENEITIES

(75) Inventors: Christopher William Gregory, Whitefish Bay, WI (US); William D. Gregory, Shorewood, WI (US)

(73) Assignee: WiSys Technology Foundation, Madison, WI (US)

( * ) Notice: Subject to any disclaimer, the term of this patent is extended or adjusted under 35 U.S.C. 154(b) by 1061 days.

This patent is subject to a terminal disclaimer.

(21) Appl. No.: 10/700,876

(22) Filed: Nov. 4, 2003

(65) Prior Publication Data

US 2004/0167421 A1    Aug. 26, 2004

Related U.S. Application Data

(60) Provisional application No. 60/424,568, filed on Nov. 7, 2002.

(51) Int. Cl.
*A61B 5/05* (2006.01)
(52) U.S. Cl. .................. 600/427; 600/428; 600/509; 600/547
(58) Field of Classification Search .............. 600/547, 600/425, 427, 428, 509; 324/228
See application file for complete search history.

(56) References Cited

U.S. PATENT DOCUMENTS 4,493,039 A * 1/1985 Gregory .................... 324/228
5,184,624 A * 2/1993 Brown et al. ............... 600/547
5,390,110 A   2/1995 Cheney et al.
5,598,185 A * 1/1997 Holmgren .................. 345/593
5,626,146 A * 5/1997 Barber et al. ............... 600/547
5,639,444 A   6/1997 Klaveness
5,651,955 A   7/1997 Klaveness
6,201,990 B1  3/2001 Wexler et al.
6,236,886 B1* 5/2001 Cherepenin et al. ........ 600/547
6,397,095 B1  5/2002 Eyuboglu et al.
6,522,910 B1  2/2003 Gregory
6,564,086 B2* 5/2003 Marchitto et al. .......... 600/425
2005/0101876 A1* 5/2005 Pearlman .................. 600/547

FOREIGN PATENT DOCUMENTS

GB   2 156 514 A    10/1985
WO   WO 02/08794 A2  1/2002

OTHER PUBLICATIONS

Seydnejad, et al; A New Method For Finding The Exact Electrode Location and Body Perimeter Used For EIT; IEEE 1994; pp. 541-542.

* cited by examiner

*Primary Examiner*—Sanjay Cattungal
(74) *Attorney, Agent, or Firm*—Quarles & Brady LLP

(57) ABSTRACT

An electrical parameter imaging apparatus and method includes the acquisition of a charge distribution pattern on an array of electrodes that surround an object being imaged. In addition the exterior boundary, or contours of the object is measured by an array of light beams and associated light sensors. The contour measurement is employed to provide a first estimate of the object geometry needed to compute an electrical parameter image from the acquired charge distribution pattern.

9 Claims, 7 Drawing Sheets

$$Q = \int V_{out}(t)/R_s \, dt$$

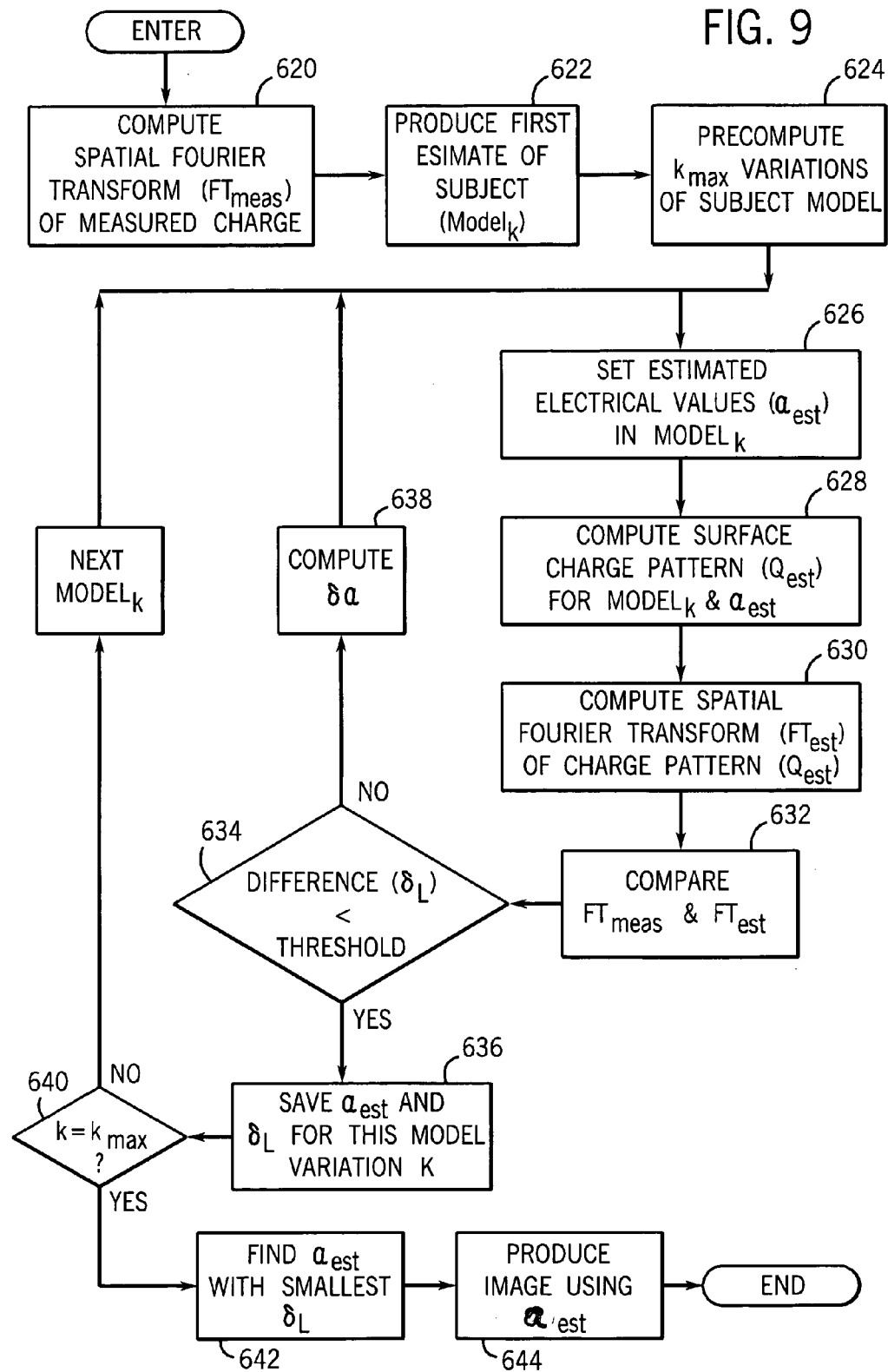

METHOD AND APPARATUS FOR PRODUCING AN ELECTRICAL PROPERTY IMAGE OF SUBSTANTIALLY HOMOGENEOUS OBJECTS CONTAINING INHOMOGENEITIES

CROSS-REFERENCE TO RELATED APPLICATIONS

This application claims the benefit of U.S. Provisional patent application Ser. No. 60/424,568 filed on Nov. 7, 2002 and entitled "METHOD AND APPARATUS FOR PRODUCING AN ELECTRICAL PROPERTY IMAGE OF SUBSTANTIALLY HOMOGENEOUS OBJECTS CONTAINING INHOMOGENEITIES".

BACKGROUND OF THE INVENTION

This invention relates to electrical imaging technology, and more specifically to an apparatus and method for producing high resolution images, with accurate values of the electrical properties of objects, such as the human breast, which are substantially homogeneous in composition except for inhomogeneities such as tumors.

The demand for new medical imaging modalities is driven by the need to identify tissue characteristics that are not currently identifiable using existing imaging modalities. After lung cancer, breast cancer remains the deadliest cancer for women, taking the lives of approximately 40,200 women in 2001 according to National Cancer Institute. There were 192,000 new breast cancer cases in 2001. Approximately 28 million women in the US are screened for breast cancer each year.

A high percentage of breast cancers are not detected at the screening stage. Studies show that 20% to 50% of breast cancers go undetected at the screening stage. The motivation for early detection is great: breast cancer detected in the early stage has an average cost of treatment of $11,000 and a 5 year survival rate of approximately 96%, while late stage breast cancer costs $140,000 on average to treat and the 5 year survival falls to 20%. Medical professionals often rely on expensive biopsies to determine cancerous tissues. These procedures are neither fast nor patient-friendly. Radiation treatment of cancerous tumors is applied broadly and excessively throughout the region of the tumor to insure complete cancerous cell destruction. Clearly, there is a need for better imaging technologies for breast cancer detection and for real-time tracking of cancer call destruction during radiation treatment procedures.

X-ray mammography is the preferred modality for breast cancer detection. With the development of digital systems, and the use of computer-aided diagnosis (CAD) that assists physicians in identifying suspicious lesions by scanning x-ray films, a large increase in mammography system sales is expected. However, as noted previously, a large number of cancers are not detected using x-ray mammography, and to reduce x-ray exposure, breast compression techniques are used which make the examination painful.

After a suspicious lesion is found, the standard procedure is to perform a biopsy. Surgical biopsy is recommended for suspicious lesions with a high chance of malignancy but fine-needle aspiration cytology (FNAC) and core biopsy can be inexpensive and effective alternatives. Both FNAC and core biopsy have helped to reduce the number of surgical biopsies, sparring patients anxiety and reducing the cost of the procedure. However, core biopsies have often failed to show invasive carcinoma and both FNAC and core biopsies can result in the displacement of malignant cells away from the target—resulting in misdiagnosis.

According to the American Cancer Society, approximately 80% of breast biopsies are benign. Because of this, new less invasive technologies have been developed including: terahertz pulse imaging (TPI); thermal and optical imaging techniques including infrared; fluorescent and electrical impedance imaging. For the most part, these technologies are being pursued as an adjunct to traditional imaging modalities including computed tomography, magnetic resonance imaging, positron emission tomography, ultrasound and hybrid systems such as PET-CT.

The biochemical properties of cancerous cells versus normal cells are characterized by three factors: increased intracellular content of sodium, potassium, and other ions; increased intracellular content of water; and a marked difference in the electrochemical properties of the cell membranes. The increased intracellular concentrations of sodium, potassium and other ions results in higher intracellular electrical conductivity. Likewise, the increased water content results in higher conductivity when fatty cells surround the cancerous cells, since water is a better conductor than fat. And finally, the biochemical differences in the cell membranes of cancerous cells result in greater electrical permittivity.

A study of breast carcinoma described three separate classifications of tissue: tumor bulk, infiltrating margins, and distant (normal) tissue. The center of the lesion is called the tumor bulk and it is characterized by a high percentage of collagen, elastic fibers, and many tumor cells. Few tumor cells and a large proportion of normally distributed collagen and fat in unaffected breast tissue characterize the infiltrating margins. Finally, the distant tissues (2 cm or more from the lesion) are characterized as normal tissue.

The characterization of cancerous tissue is divided into two groups: in situ and infiltrating lesions. In situ lesions are tumors that remain confined in epithelial tissue from which they originated. The tumor does not cross the basal membrane, thus the tumor and the healthy tissue are of the same nature (epithelial). The electrical impedance of an in situ lesion is thus dependent on the abundance of the malignant cells that will impact the macroscopic conductivity (which is influenced by the increase in sodium and water) and permittivity (which is influenced by the difference in cell membrane electrochemistry).

By contrast, infiltrating lesions are tumors that pass through the basal membrane. The malignant tissue has a different nature than normal tissue (epithelial vs. adipose). Epithelial tissue is compact and dense. Adipose tissue is composed of large cells that are mostly triglycerides. These structural differences have the following impact. First the normal tissue has a lower cellular density. Second, cell liquid of normal tissue is not as abundant as epithelial cells. Generally the radiuses of epithelial cells are less than adipose cells, from which we conclude that the radius of cancerous cells is less than for normal cells. The impact on the fractional volume of cancerous cells vs. normal cells is that the fractional volume of cancerous cells is greater than for normal cells. The reason is that the epithelial population is higher than for normal, adipose cells. Finally, we note that intracellular conductivity of cancerous cells is greater than for intracellular conductivity of normal cells. Also, extracellular conductivity is higher because of the abundance of the extracellular fluid (because of larger gaps between normal and cancerous cells). Thus, the conductivity of the infiltrated tissue will be greater than for normal tissue.

Since the 1950's several researchers have measured and tabulated the electrical properties of biological tissues. The electrical properties (conductivity and permittivity) of human tissues exhibit frequency dependence (dispersion). There are three dispersion regions ($\alpha$, $\beta$, and $\gamma$) at frequencies ranging from D.C. to 1 GHz. These dispersions in tissues are dependent on the number of cells, the shape of the cells, and their orientation, as well as the chemical composition of the tissue (i.e. composition and ionic concentrations of interstitial space and cytoplasm).

Various studies show that the values of biological tissues resistivities vary for a host of reasons. Cancerous tumors, for instance, possess two orders of magnitude (factor of 100) higher conductivity and permittivity values than surrounding healthy tissue. The application of medical treatments also produces a change in the electrical properties of tissue. For muscle tissue treated with radiation measurable changes to tissue impedance is reported. Significant changes occur in electrical impedance of skeletal muscle at low frequencies during hyperthermia treatment, and this change of electrical properties foreshadows the onset of cell necrosis.

Electrical impedance tomography (EIT) is a process that maps the impedance distribution within an object. This map is typically created from the application of current and the measurement of potential differences along the boundary of that object. There are three categories of EIT systems: current injection devices, applied potential devices, and induction devices. Henderson and Webster first introduced a device known as the impedance camera that produced a general map of impedance distribution. The Sheffield System and its incarnations were the first generation EIT system. In the later 80's, Li and Kruger report on an induced current device. In such a system, a combination of coils is placed around the object under test. A changing current in the coils produces a varying magnetic field that in turn induces a current in the object under test. As with the other drive method, electrodes are placed on the boundary of the object to measure the potential drops along the boundary.

Such electrical property imaging techniques are often referred to as "impedance tomography." Most conventional electrical property imaging techniques are based on the premises that: 1) electrodes, or sensors, should be attached directly to the sample to be measured (for medical applications, the sample is a human body), and 2) current is injected sequentially through each electrode into the sample and the subsequent voltages measured. Therefore, these conventional imaging techniques implement a "constant current/measured voltage" scheme.

In a departure from such conventional electrical property imaging techniques, one of the present inventors arranged sensors in an array outside the object to be measured as disclosed in U.S. Pat. No. 4,493,039. Further, during imaging of a sample, ac voltages were applied at a fixed amplitude while the current was measured. This approach was further improved as described in pending patent application WO 99/12470 by filling the space between the object and the sensor array with an impedance matching medium. In addition, two techniques for computing the internal charge distribution based on the measured surface charges are described, referred to as the scale factor technique and the iterative technique. Both the iterative and scale factor technique require initial estimates of the geometry of internal structures derived from an associated imaging system such as an x-ray CT system. The iterative technique also requires an initial guess of the electrical properties of each region, and a forward calculation of the expected currents at the boundary to check the validity of the guess is then performed. This process is iterated until the guess produces boundary currents close to the measured values. The scale factor technique creates a "look up" table or neural net algorithm that allows one to correlate electrical properties or the interior of the sample with externally measured parameters using a large data set of model calculations. Because of limitations of the model and the need to extrapolate results to keep the size of the data sets reasonable, the scale factor technique has limited accuracy, but it does not require prior knowledge of approximate sample electrical properties. In fact, the results of the scale factor computation may serve as an initial estimate for the iterative technique. Both techniques are computationally intensive.

SUMMARY OF INVENTION

The present invention solves the problems associated with prior electrical parameter imaging techniques by providing an apparatus and method that generates an accurate image of the electrical properties of an object without the need for excessive computation time and without the need for initial estimates based on a CT or MRI image.

More specifically, when imaging an object, such as the human breast, which has a substantially homogeneous structure, the location of the outer boundary of the object is detected in addition to the charge accumulated at that boundary when known voltages are applied. With the shape of the exterior boundary of the object known, the electrical property imaging procedure may be employed with an initial estimate of properties throughout the object. Anomalies, such as tumors, are seen as an extra contribution to the accumulated charges on the sensors and these extra charge contribution can be used to locate the position of internal anomalies and measure their size and electrical properties.

A general object of the invention is to provide an electrical property imaging method and system which enables an image of electrical properties to be produced without the need for a separate tomographic image. The location of the object peripheral boundary is detected using arrays of optical sources and sensors that are interleaved with the electrical property measurement sensors. The object boundary is thus located and automatically registered with the charge measurements made by the electrical property sensors.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

FIG. 9 is a flow chart of an image reconstruction program performed by the computer controller of FIG. 5.

DESCRIPTION OF THE PREFERRED EMBODIMENT

Figure 2:
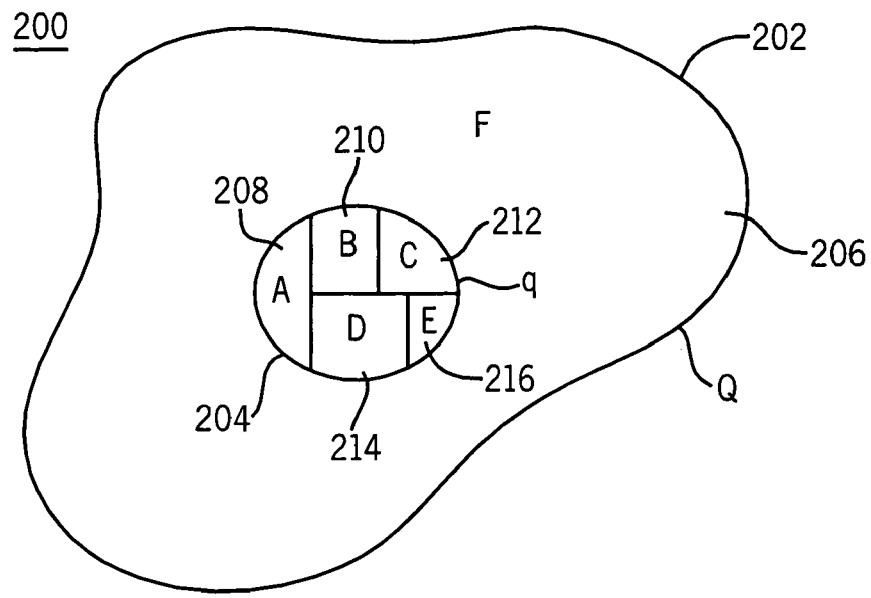
FIG. 2 is a planar view of a closed volume in space.

The underlying mathematical theory of the imaging technique of the present invention will now be described with reference to FIGS. 2-4. FIG. 2 is a planar view of a closed volume space 200 surrounded by a surface 202 that contains a sample 204 and an interior region F 206, such that region F 206 is the space between the sample 204 and the surface 202. The sample 204 comprises a plurality of connected subregions which for convenience are labeled: subregion A 208, subregion B 210, subregion C 212, subregion D 214, and subregion E 216. Each subregion 208-216 may be composed of a different material, such as different tissues in a human subject.

When an electromagnetic field at some specified frequency (f) is applied to the sample 204 in the closed volume space 200, a total charge is produced only where the electrical properties change, such as at the boundaries between each subregion 208-216 of the sample 204 where there is a dissimilarity in the dielectric constant and conductivity electrical properties of each subregion 208-216. These total charges will in turn induce a redistribution of the total charges on the surface of the closed volume space 200. It is assumed that these induced charge distributions result from both free charges (free to move individually) as well as polarization charges located on the surface 202 of the closed volume space 200. The charges on the surface 202 are also total (free plus polarization) charges wherein the total charge on a point on the surface 202 is indicated with a capital "Q", while the total charge on a point in the interior of the closed volume space 200 is indicated with a small "q." It is important to note that the measurement of the total charge Q can involve either an actual measurement of the charge Q or the charge Q as derived from a small increment of the electrical current, I, which is the rate of change of the charge Q with time.

The total charge Q at a point on the surface 202, and the total charge q at a point in the interior can be connected via electromagnetic theory. When time varying electric fields are applied to electrical media they induce currents in the media. These currents in turn produce time varying magnetic fields that can add induced electric fields to the applied electric field via Faraday's law. This extra contribution to the electric field is negligible at low frequencies and can be ignored. We will use this so-called quasi-static approximation. The fundamental theorem of electrostatics shows that an interior total charge q and a total charge Q on the surface 202 are uniquely related.

Figure 3:
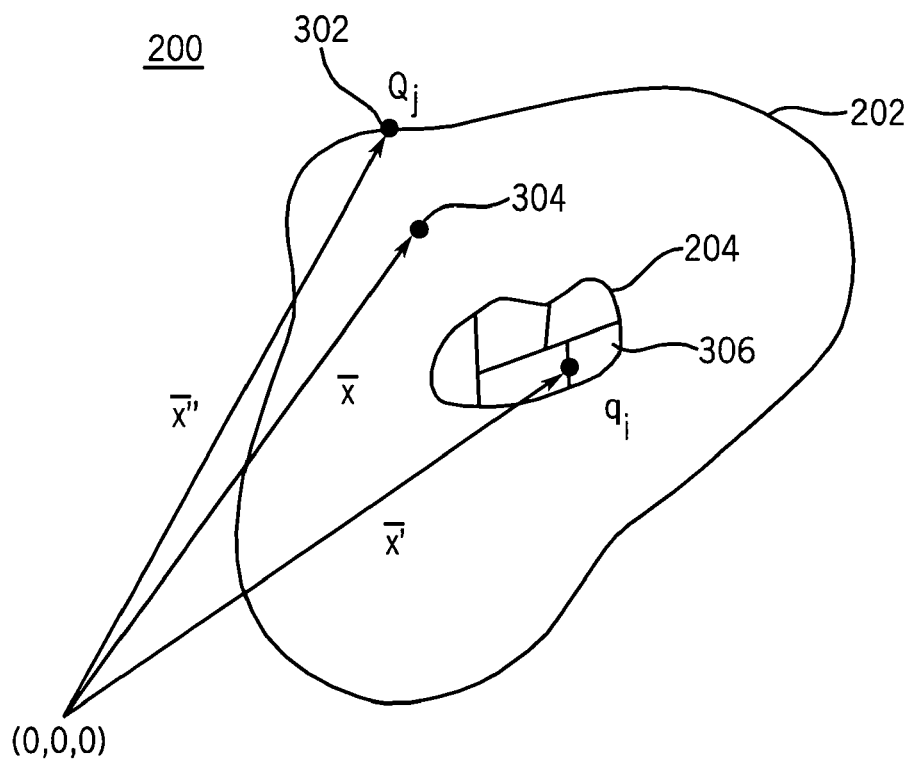
FIG. 3 is a planar view of a closed volume in space showing the relationship between the measured exterior total charges $Q_j$ and the interior total charges $q_i$.
Figure 4:
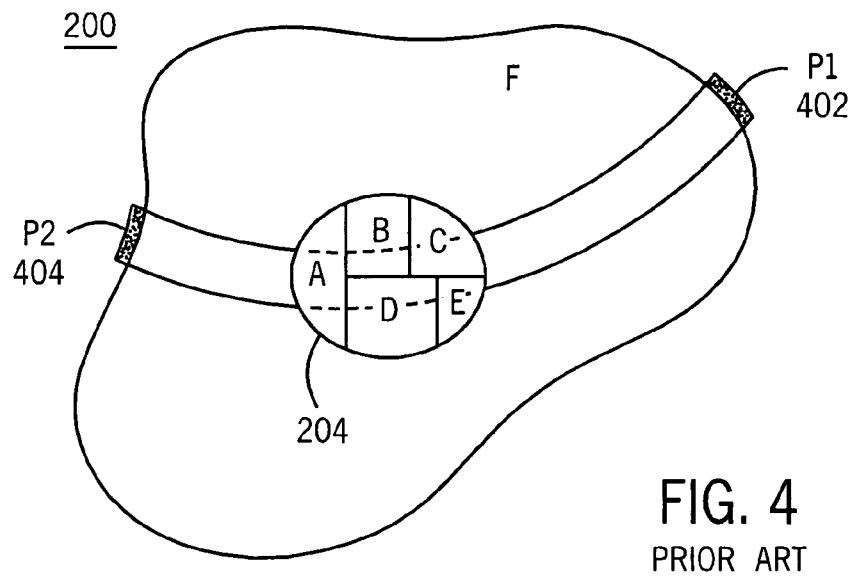
FIG. 4 is a planar view of a closed volume in space being measured by a conventional electrical property imaging technique.

FIG. 3 is a planar view of the closed volume space 200 showing the relationship between the total charge Q at a point 302 on the surface 202 and a total charge q at a point in the interior that are connected via The Greens Function. Specifically, The Greens Function connects a total charge Q on the surface 202 at point j with an interior total charge q at point i:

$$q_i \leftrightarrow Q_j$$

This relationship provides the desired information about the electrical properties of the interior subregions 208-216 of sample 204. FIG. 3 illustrates the coordinate system and some of the relevant geometry used in this discussion. The notation used in the coordinate system for the field point 304, the source point 306 and surface point 302 are X, X prime (X'), and X double prime (X") respectively. By associating the total charges q inside the sample 204 at the source point 306 with the total charges Q at the surface point 302, an enhanced image of the interior of the sample 204 can be generated. Therefore, the position at which the electric field is measured is field point 304.

The imaging technique of the present method differs significantly from the conventional electrical property imaging techniques. FIG. 4 is a planar view of a closed volume space 200 being measured by such conventional imaging techniques. The electrical properties of the sample are represented by a network of lumped circuit elements. With such a method, currents are injected at known places, e.g., P1 402, on the surface 202 of the closed volume space 200 and extracted at known places, e.g., P2 404. The voltages on the surrounding sensors are then measured and the lumped circuit impedances are computed from the set of current-voltage measurements. In contrast, the technique of the present invention allows one to fully describe the wave-like nature of the electric fields in the closed volume space 200 and the measuring volume and does not require any specific assumption regarding the structure of a lumped circuit element network or of the equivalent circuits used to characterize the subregions 208-216 of the sample 204 being measured.

Applying the Maxwell Equations of electromagnetic theory to the problem as just described results in Equation 1A:

$$\nabla \cdot [(\sigma + j\omega\epsilon_0\epsilon_r)(-\nabla\Phi)] = 0 \tag{1A}$$

where:

$\sigma$=conductivity $\epsilon_r$=relative dielectric constant $\epsilon_0$=dielectric constant of free space $\Phi$=potential.

In addition, a standard result of electromagnetic theory is the connection between the potential, ($\Phi$), and the total charge density, $\rho$, known as the Poisson Equation, Equation 1B:

$$\nabla^2[\Phi] = \frac{\rho_{Total}}{\varepsilon_0} \tag{1B}$$

where $\rho_{Total}$ is the volume total charge density. The field E is obtained from the following equation:

$$E = -\nabla\phi \tag{1C}$$

The Equations 1A and 1B show that the scalar potential phi ($\phi$), the charge densities that are important are related to the total charge, i.e., the free charge plus polarization charge.

Other methods for imaging the electrical properties attempt to compute the dielectric constant and conductivity of each region directly from the measurements. We compute the total internal charges as an intermediate step. One advantage of seeking the charges rather than going directly for the conductivity or dielectric constant is that one can see that the internal charges, which totally govern the electrical picture, appear essentially only at boundaries that exist at discontinuities within the object, thus there are far fewer values to compute. Equation 2 below shows this since the gradient of the conductivity and the gradient of the dielectric constant contribute to the total charge density. Therefore, total charge depends on the rate with which the conductivity and the dielectric constant change with distance.

$$\rho_{Total} = \frac{[\nabla\sigma + j\omega\nabla(\varepsilon_0\varepsilon_r)] \cdot \nabla\Phi}{\sigma + j\omega\varepsilon_r}(\varepsilon_0) \quad (2)$$

A standard theorem in electromagnetic theory is the Uniqueness Theorem. The Uniqueness Theorem for the quasistatic case states that if the potential or its normal derivative is known on a surface surrounding a closed volume, then the potential at a field point 304 can be uniquely determined. It is important to note that both the potential and the normal derivative of the potential need not be known. In fact, the problem would be over determined if both were known. While it is possible to define the problem with the potential known on some portion of the bounding surface and the normal derivative on other portions, Equation (3) below considers the simple case where the potential on the surface 202 is known. This is known as the Dirichlet boundary condition.

Equation 3 is the solution to Poisson's Equation (Equation 2) using the Green's Function.

$$\Phi(\overline{X}) = \frac{1}{4\pi\varepsilon_0}\int \rho_{Total}(\overline{X}')xG_D(\overline{X},\overline{X}')d\tau - \quad (3)$$

$$\frac{1}{4\pi}\oint \Phi(\overline{X}')\frac{\partial G_D(\overline{X},\overline{X}')}{\partial n'}dS$$

Where $G_D$ is the Dirichlet Green's Function, $d\tau$ is an element of volume and S is an element of surface surrounding the volume $\tau$.

Equation 3 is the potential at the field point 304 as determined by the total charge q on the interior and the potential on the surface 202, exactly as the Uniqueness Theorem predicts. The solution is obtained in the terms of a geometrical function, the Green's Function, which is a standard treatment. When a sample 204 is present, both the volume integral over the total charge q density and the surface integral over the surface 204 are present. If the same potential distribution on the surface is considered but with no sample present, then the charge density goes to zero but the surface integral remains the same. The surface term (the second integral in Equation 3) is unchanged by inserting the sample 204 because the voltage is set to pre-determined values on the surface 202 and kept at those values before and after inserting the sample 204. Because of this, when the two terms are subtracted, the remaining expression involves only the Green's Function (which is a known quantity for a given shape of the array of measuring sensors) and the charge density. Therefore, it is convenient to use the difference in the potential between the case when a sample 204 is inserted and when a sample 204 is not inserted between the sensors. This potential difference can be related to the charges at the surface 202 by taking the normal derivative of the potential difference to produce the normal component of the electric field since, by Gauss's law, the normal component of the field near a conducting surface is directly proportional to the charge per area on that surface. We then change from a continuum model to a sum over discrete charges and Equation (4) below then shows that those charges $Q_j$ at the surface 202 labeled by the index "j" will be related to the charges $q_i$ on the interior labeled by the index "i" by a matrix element involving both "j" and "i" wherein the connecting matrix element is simply the normal derivative of the Green's Function:

$$\delta_{Q_{jTotal}} = Q(i)_{Total}^{Full} - Q(i)_{Total}^{Empt} = \sum q_{iTotal}\frac{\partial G_D(j,i)}{\partial n_j''} \quad (4)$$

Equation 5 shows that this series of equations in "j" can be written down and grouped together in matrix formulation involving a charge on the surface 202 as a vector, with each term of the vector one of the total charges. For the charges on the surface 202, a capital "Q" is used and they are related to a similar vector for which each term is one of the total charges on the interior using the small "q".

$$\overline{\delta_Q} = \overline{\delta_q} \cdot \overline{\frac{\partial G_D}{\partial n_n''}} \quad (5)$$

This series of equations is inverted to give the charges on the interior, "q", provided that the matrix itself has an inverse. More specifically, the Green's Function derivative matrix is multiplied by its inverse, resulting in a unit matrix if an inverse exists as shown in equation(6).

$$\overline{\frac{\partial G_D}{\partial n}} \cdot \left(\overline{\frac{\partial G_D}{\partial n}}\right)^{-1} = I = \begin{pmatrix} 1 & 0 & . & . & 0 \\ 0 & 1 & 0 & . & . \\ . & 0 & 1 & . & . \\ . & . & . & 1 & 0 \\ 0 & . & . & 0 & 1 \end{pmatrix} \quad (6)$$

As will be described in more detail below, the subject to be imaged is placed in a measurement array which enables a sinusoidal voltage of a desired frequency and 15 or less volts rms to be applied to the surface of the subject to establish an electric field $\overline{E}$ through the subject. The surface charges $Q_j$ that result from this applied field are measured. The surface charge measurement may be repeated with the applied electric field oriented in different directions and it may be repeated at different frequencies from 10 KHz to 10 MHz.

Equation 7 below shows how to reduce the double sum that appears in the expression for the total charge $Q_j$ on the surface of the subject to a single sum. The Green's Function is expanded in a complete set of orthogonal functions (which is just the sine function), the result is a sum over the parameter "L" which appears inside the sine function in Equation 7 and also a sum over the charges $q_i$ which appear in Equation 4. Multiplying the appropriate sine function for given value "L", and summing up over one side of the measurement array, the sum over "L" is eliminated, thereby leaving just one term. This result occurs because of the orthogonality property of sine and cosine functions. The accuracy can be further improved by adding the results from corresponding measurements on opposite sides of the measurement array resulting in the equation for a given value of "L" for the Fourier Transform (the sine transform) as shown in Equation 8.

$$FT(L) = \int_0^a [\delta Q_{Top}(x) + \delta Q_{Bottom}(x)]\sin\left(\frac{L\cdot\pi\cdot x}{a}\right)dx \quad (7)$$

-continued $$FT(L) = \frac{|\Delta S|}{\pi^2} \sum_i \frac{q_i \cdot \sin\left(\frac{L \cdot \pi \cdot x_i'}{a}\right) \cdot \cosh\left(\frac{L \cdot \pi \cdot \left(\frac{b}{2} - y_i\right)}{a}\right)}{\cosh\left(\frac{L \cdot \pi \cdot b}{2a}\right)} \quad (8)$$

The procedure now is relatively simple. For each value of "L", one equation can be produced each of which involves the sum over the charges labeled by "i," the matrix elements of which are shown in Equation 8.

Using the iterative process described below, an accurate representation of the charges q in the interior of the object can be determined. Once this has been done, the interior charge distribution image can be used to build the solution for the potential everywhere on the interior of the object using the known Green's Function Solution presented in Equation (3) above. Once the potential everywhere on the interior of the object is known, the electrical fields can be easily generated from those potentials using Equation (1C). One can then obtain the change in the electrical field as you go from one point in the interior to another, which then produces an estimate of the electrical properties at every point in the interior of the object.

The final steps in taking the interior measured charges and producing the potentials and/or electrical fields on the interior of the object can be accomplished by inserting the charges q into the Greens' functions solution Equation (3). We note that there are two terms in the expression for the interior electrostatic potentials: A) volume integral involving the charges q that were just calculated above and B) integral over the surface involving known potentials that are set at the surface. The first integral is obtained just using the charges calculated above. The second integral is obtained just as easily, because the potentials that are set at the surface sensors are determined by the experimenter and are known. Therefore everything is know and can be calculated by a simple plug-in operation and known formula to get the interior potentials according to equation (3).

Once the interior potentials are known, the electric field everywhere can be obtained from the rate of change of the potential in each direction as given in Equation (1C). Once the electric fields are known everywhere in the interior the electrical properties ($\sigma$ and $\epsilon_r$) of each region within this object can be computed from the change of the normal component of this electric field across each boundary within the object. Therefore, by starting with the known electrical properties of the medium surrounding the object, the electrical properties of adjacent regions in the object can be calculated. At each boundary of region(n) to region (n+1) the ratio of the normal components of the electric fields are related to the electrical properties in regions (n) and (n+1) as follows:

$$E(n)_{normal}/E(n+1)_{normal} = (\sigma + j\omega\epsilon_r \epsilon_0)[n+1]/(\sigma + j\omega\epsilon_r \epsilon_0)[n]. \quad (9)$$

Since the values of $\sigma$ and $\epsilon_r$ are known for the medium surrounding the subject, use of Equation (12) will yield corresponding values for the next region (n=2). Applying the equation again for the boundary between region 2 and 3, we get the values for region 3, and so on until we have the electrical properties of the entire object. When imaging the breast, for example, the electrical properties of the surrounding saline solution medium are known and the process is applied to calculate the electrical properties of any anomalous regions in the breast. It is the electrical characteristics of these anomalous regions which indicate the nature of the tissue and the presence of a malignant tumor.

Figure 5:
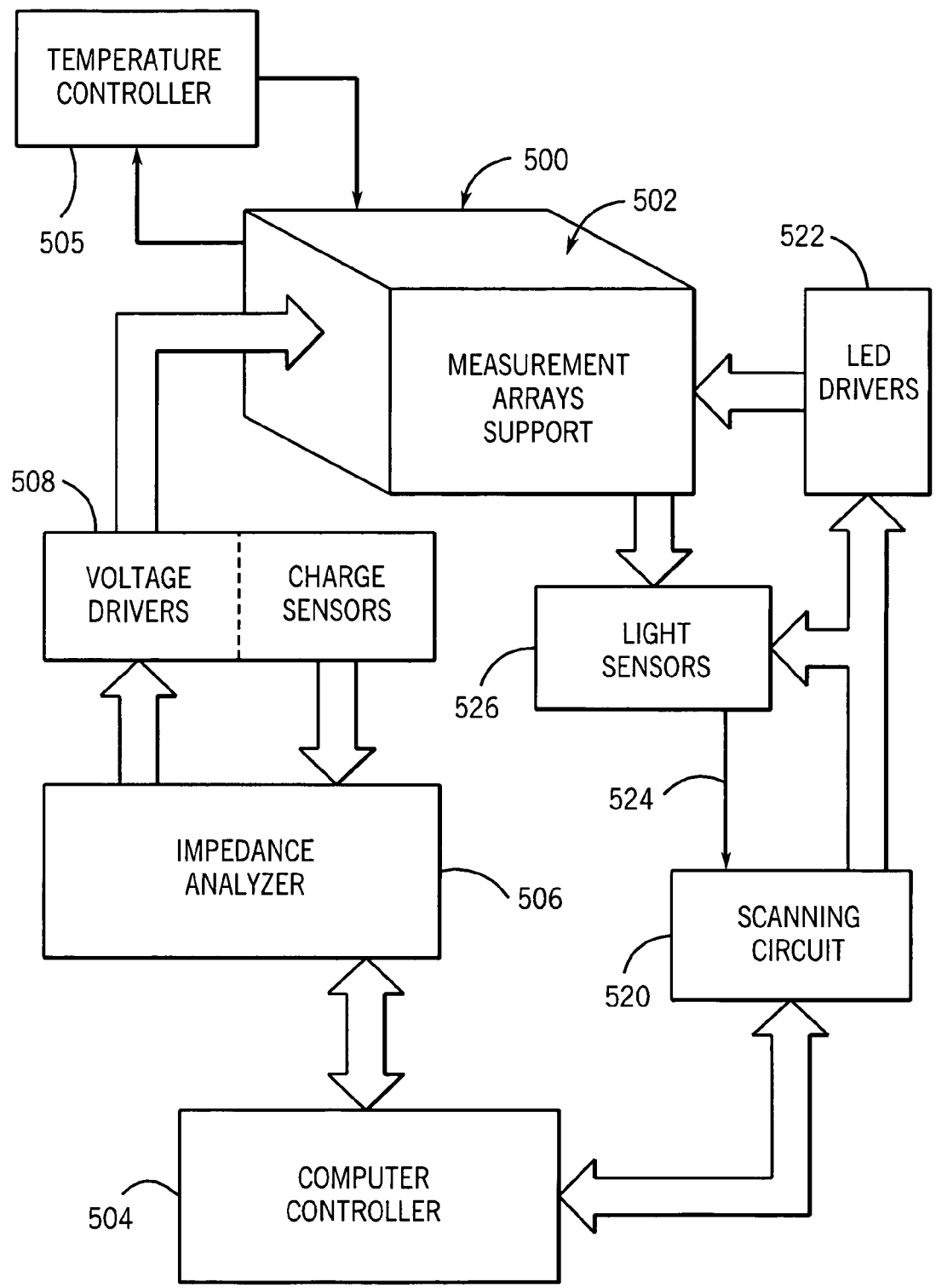
FIG. 5 is a block diagram of the preferred embodiment of an electrical properties imaging system which employs the present invention.

The system for acquiring the surface charge data and subject contour data and producing therefrom an image indicative of the electrical characteristics of the subject is shown in FIG. 5. It includes a measurement array support structure 500 that is illustrated in more detail in FIGS. 7A and 7B and described in detail below. The support structure 500 has four vertical sides and a bottom which forms a container that is filled with a saline water solution of known electrical properties that are matched as closely as possible to the electrical properties of the subject. The subject to be imaged is inserted through the open top 502. When used to image the breast, the support structure 500 is mounted beneath an opening in a patient table and the breast is aligned to hang down into the container.

The system is controlled by a computer controller 504 which is shown in more detail in FIG. 1 and described below. It operates an impedance analyzer 506 to apply voltages to the separate elements of a charge measurement array through voltage drivers 508, and it measures the resulting charge Q at each of these elements. The impedance analyzer 506 is commercially available from Solartron Analytical under the trade name "1260 Impedance/Gain Phase Analyzer". It is operated using its "Z plot" software that is run on the computer controller 504.

Figure 6:
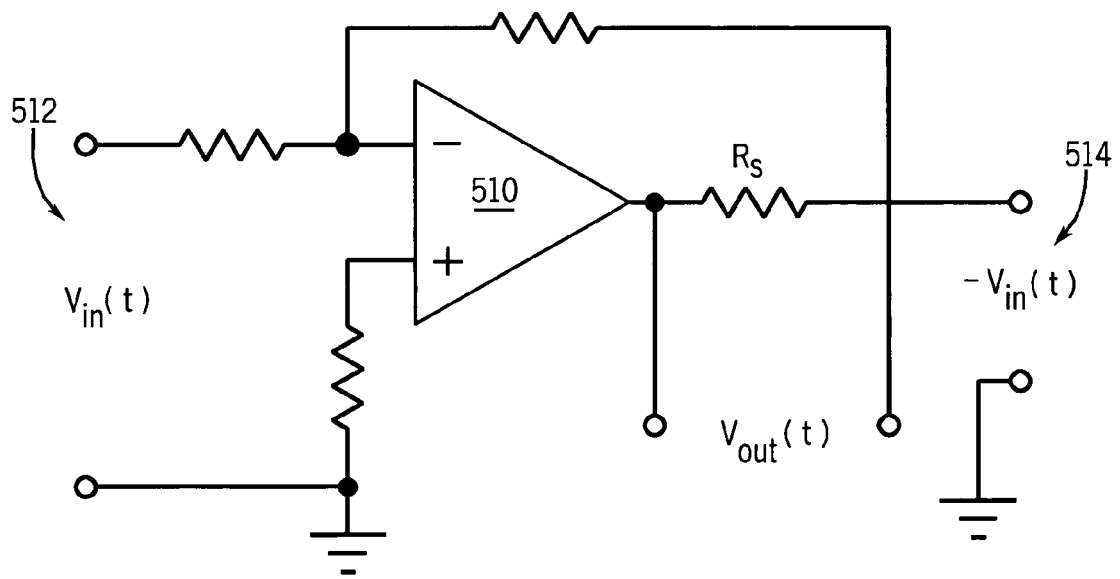
FIG. 6 is a circuit diagram of a voltage driven circuit which forms part of the system of FIG. 5.

The voltage drivers and charge sensors are shown in detail in FIG. 6. The operational amplifier 510 is operated as an inverter with unity gain between its input terminals 512 and a pair of outputs 514 that connect to a charge measurement array element. The voltage drop across a series connected output resister $R_s$ serves as the output to the analyzer 506 and is used to calculate the resulting surface charge $Q_j$ at the charge measurement array element to which the outputs 514 connect.

The computer controller 504 also operates a scanning circuit 520 to acquire data which indicates the surface contour of the subject being imaged. The scanning circuit 520 sequentially enables LED driver circuits 522 to sequentially energize LEDs in LED arrays disposed along two sides of the support structure 500. Simultaneously, a signal is input at 524 from a corresponding, enabled, light sensor in light sensor arrays 526 disposed along the two opposing sides of the support structure 500. By sequentially enabling pairs of LED drivers 522 and corresponding light sensors 526, the contour of the subject in the support structure 500 can be determined. The scanning circuit 520 provides a map to the controller 504 which indicates the light paths that are blocked by the subject in the support structure 500. A program performed by the controller 504 interpolates this map data to define the outer surface of the subject being imaged.

To maintain the accuracy of the measurements it is necessary to control the temperature of the saline solution in the measurement array support structure 500. This is accomplished by a temperature controller 505 which operates a heating element (not shown) in the support 500 in response to a signal received from a temperature sensor (not shown) which is also in the support 500. Preferably, the temperature is maintained at body temperature for the comfort of the patient.

Figure 7A:
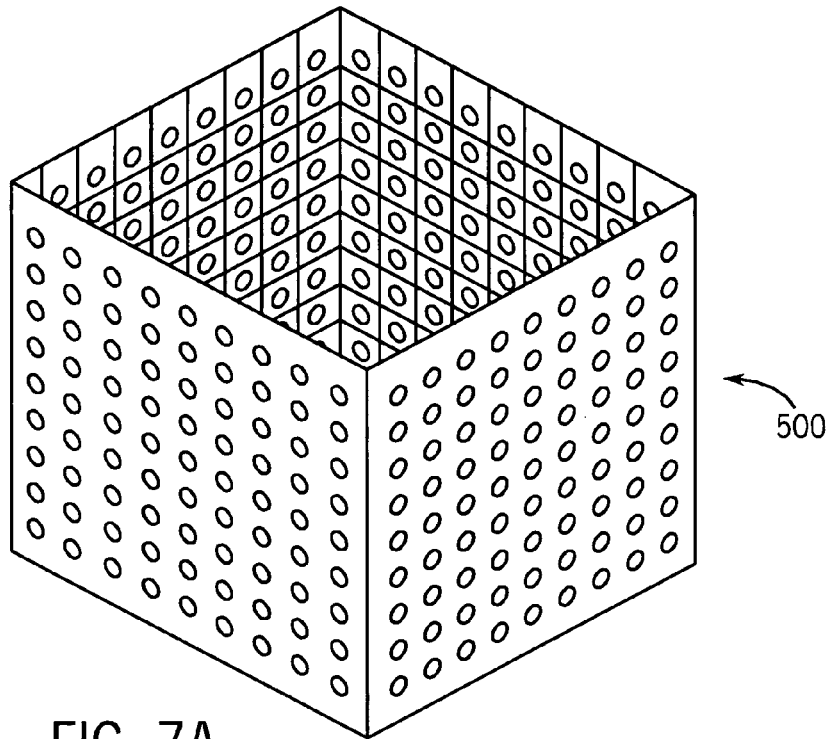
FIG. 7 is a schematic diagram of the measurement array support which forms part of the system of FIG. 5.
Figure 7B:
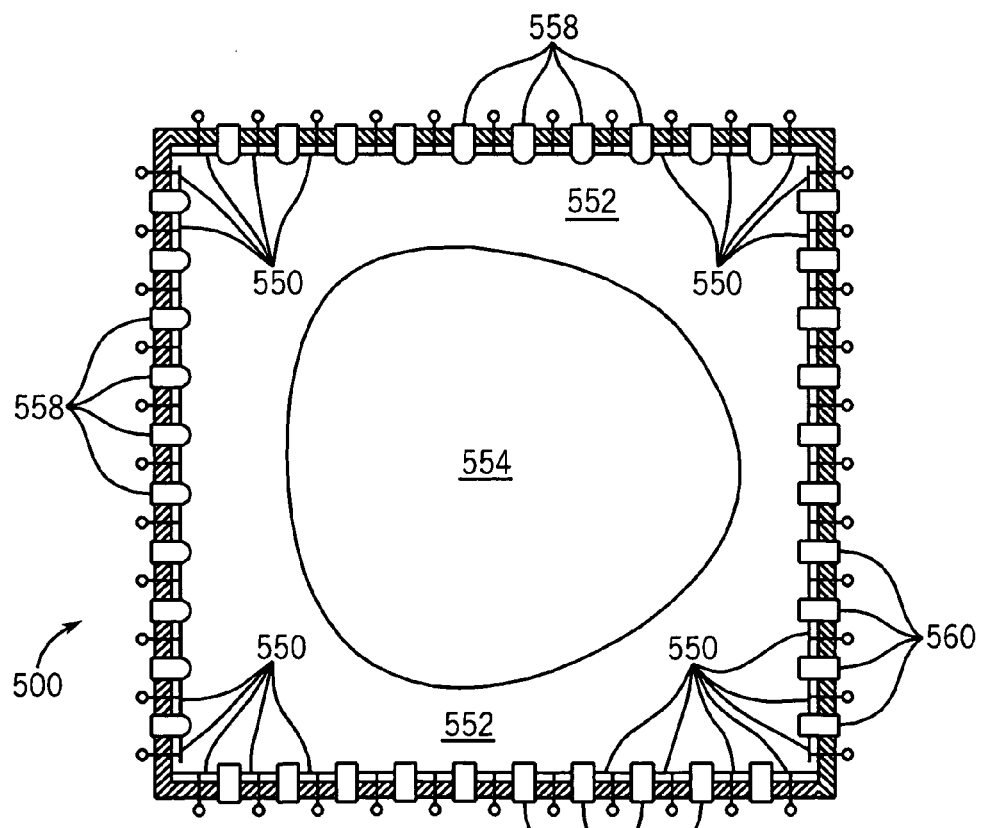

Referring particularly to FIGS. 7A and 7B, the measurement arrays support structure 500 includes 2D arrays of metal elements 550 disposed on all four sides of the container. These elements 550 are square metal electrodes that connect to the outputs 514 of corresponding voltage drivers 508. They are in electrical contact with the saline solution medium 552 that surrounds the subject 554. The voltages applied to these elements 550 establish an electric field E within the container and throughout the subject 554, and they accumulate a surface charge $Q_j$ that is dependent on the electrical characteristics of the subject 554. In the preferred embodiment 225 elements 550 are disposed on each of the four sides and they are constructed of silver with a silver chloride coating.

Two-dimensional arrays of light emitting diodes 558 are disposed in two adjacent walls of the support structure 500 and two-dimensional arrays of light sensors 560 are disposed in the two opposing walls. Each LED 558 is paired with a corresponding light sensor 560 disposed on the opposite wall to define a unique light path through the container. By sequentially enabling each pair as described above, all of the light paths through the container can be systematically examined to determine which ones are blocked by the subject 554. In order to more accurately measure the contour, the entire support structure 500 may be rotated to acquire contour data from a number of different views.

Figure 1:
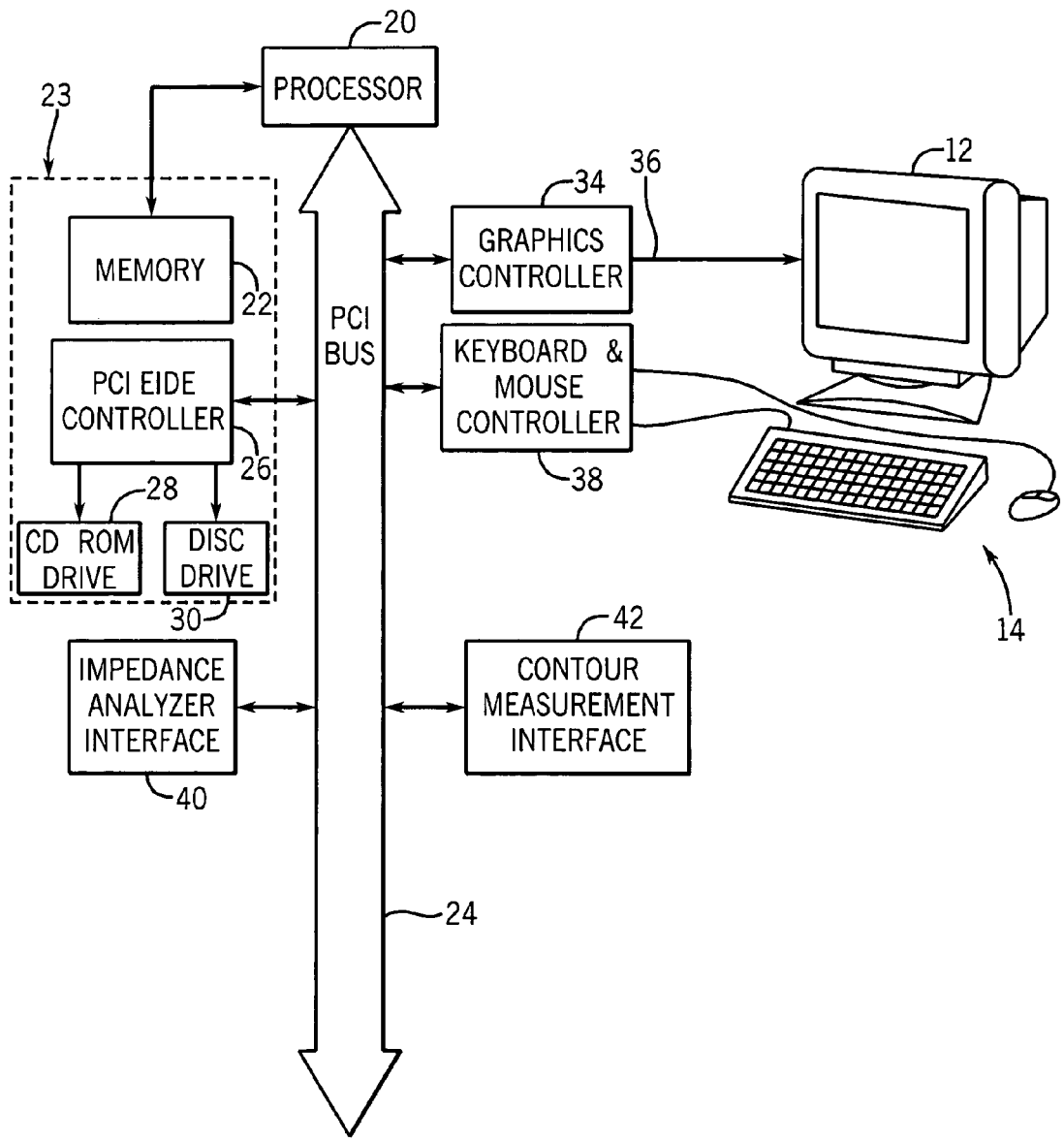
FIG. 1 is a block diagram showing an exemplary computer system useful for implementing the present invention.

Referring particularly to FIG. 1, a computer controller system includes a processor 20 which executes program instructions stored in a memory 22 that forms part of a storage system 23. The processor 20 is a commercially available device designed to operate with one of the Microsoft Corporation Windows operating systems. It includes internal memory and I/O control to facilitate system integration and integral memory management circuitry for handling all external memory 22. The processor 20 also includes a PCI bus driver which provides a direct interface with a 32-bit PCI bus 24.

The PCI bus 24 is an industry standard bus that transfers 32-bits of data between the processor 20 and a number of peripheral controller cards. These include a PCI EIDE controller 26 which provides a high-speed transfer of data to and from a CD ROM drive 28 and a disc drive 30. A graphics controller 34 couples the PCI bus 24 to a CRT monitor 12 through a standard VGA connection 36, and a keyboard and mouse controller 38 receives data that is manually input through a keyboard and mouse 14.

The PCI bus 24 also connects to an impedance analyzer interface card 40 and a contour measurement interface card 42. The interface card 40 couples data to and from the impedance analyzer 506 during the data acquisition phase of the procedure. A program executed by the processor 20 controls the impedance analyzer 506 to apply voltages to the charge measurement array and to input data indicative of the resulting surface charge $Q_j$. The interface card 42 connects to the scanning circuit 520 that drives the array of light emitting diodes (LEDs) and receives responsive signals from the corresponding array of light sensors. A program performed by the processor 20 controls the scanning circuit 520 through the interface card 42 to measure the contour of an object placed in the support structure 500 and inputs data through the interface card 42 that indicates the surface boundary of the subject being imaged.

Figure 8:
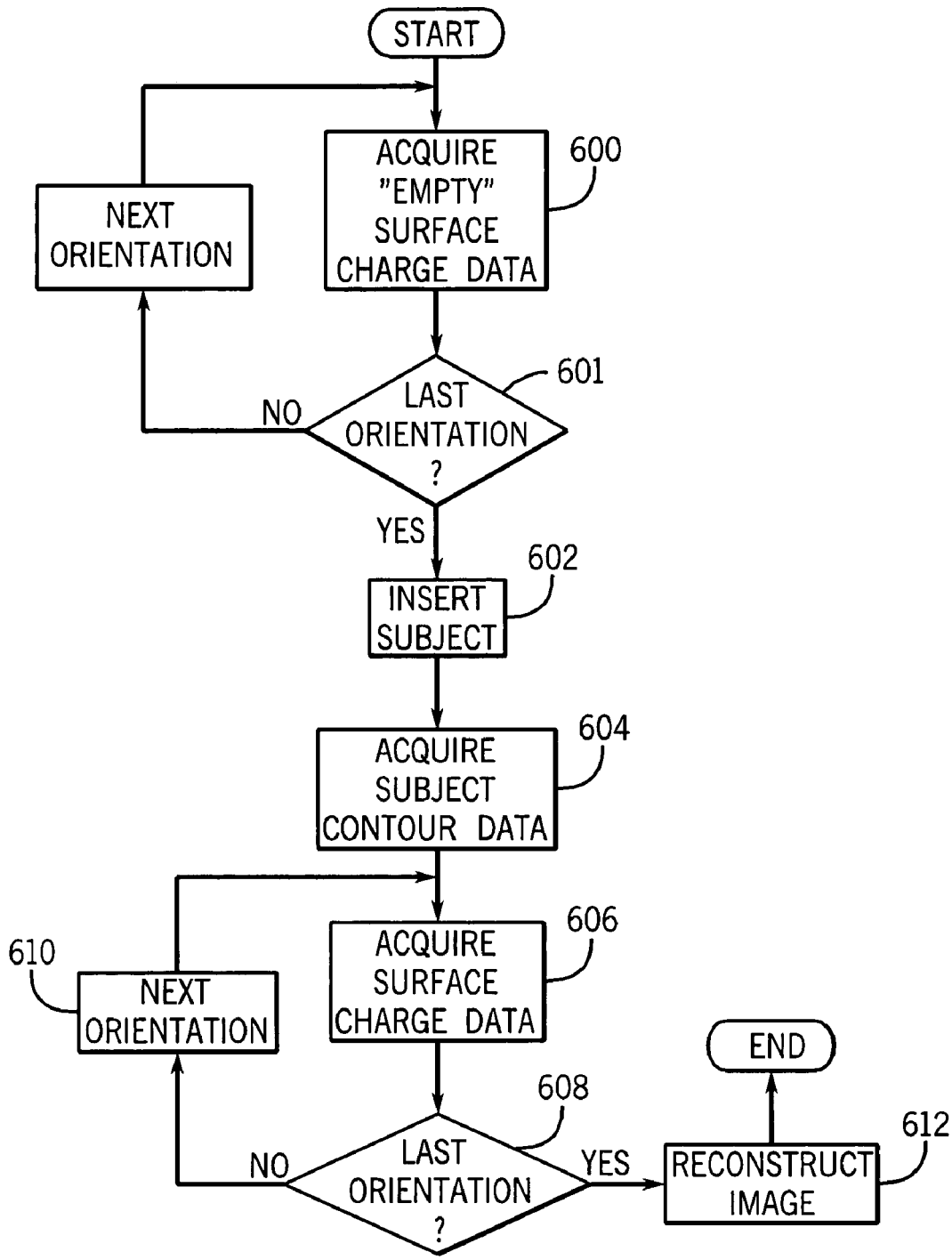
FIG. 8 is a flow chart of a data acquisition program performed by the computer controller in FIG. 5.

Referring particularly to FIG. 8, the procedure is comprised of an image acquisition phase and an image reconstruction phase. As indicated by process block 600, the first step in the image acquisition phase is to acquire surface charge data $Q_j$ without the subject in place. This "empty" surface charge data is needed during the reconstruction phase and it is acquired by applying voltages at a selected frequency to the measurement array 500 as described above. The resulting surface charge $Q_j$ that accumulates over a finite time interval are input. The system loops back at decision block 601 to collect charge data at all possible orientations of the applied E field.

The subject is then inserted into the measurement array support structure 500 as indicated at process block 602 and the contour of the subject is measured as indicated at process block 604. As described above, this includes the acquisition of a map which indicates the light paths that are blocked by the subject. This input data is interpolated to define the location and contour of the outer surface of the subject.

A loop is then entered in which the surface charge data $Q_j$ is acquired at the prescribed frequencies and the prescribed E field orientations. The surface charge data $Q_j$ is acquired at process block 606 by applying voltages to the charge measurement elements 550 at the prescribed frequency and reading the charges $Q_j$ that accumulate at each element 550. The measurement is repeated at each prescribed frequency. As indicated at decision block 608, the system then loops back to repeat these measurements at other E field orientations. As indicated at process block 610, the voltage amplitudes applied to the charge measurement elements 550 are changed to reorient the direction of the electric field E that is produced in the subject. At least three acquisitions at different E field orientations are needed to provide 3D information and further acquisitions may be acquired to improve the SNR of the final image. When the surface charge data has been acquired for the last E field orientation as determined at decision block 608, the image reconstruction can begin as indicated at process block 612.

Referring particularly to FIG. 9, image reconstruction begins by computing the spatial Fourier Transform of the acquired surface charge data $Q_j$ ($FT_{meas}$) as indicated at process block 620. The next step as indicated at process block 622 is to produce a first estimate of the physical location, shape and size of the subject and any anomalies therein. This first physical estimate (model$_k$) is produced using the acquired subject surface contour data and assigning "normal" tissue electrical property values to all locations inside the subject. Anomalies such as tumors are estimated by comparing the measured charge distribution $Q_j$ on the subject and the expected surface charge distribution calculated based on normal tissue throughout. The difference between these expected surface charge distributions and the measured charge distributions provides the information needed to locate anomalies in the otherwise homogenous electrical characteristics of the subject.

The next step as indicated at process block 624 is to pre-compute a range of possible variations in this initial physical model of the subject (model$_k$). These variations typically include variations in the size, shape and location of the estimated anomalies. As will be described below, each of these $k_{max}$ physical models will be used to find the optimal electrical characteristic image.

An iterative process is then begun in which the electrical characteristic image which best "fits" the measured charge ($FT_{meas}$) is produced. First, as indicated at process block 626 the electrical values ($\alpha_{est}$) of the subject tissues, including anomalies, are estimated using the physical model$_k$ and the measured charges Qj. Using the physical model$_k$ and the estimated electrical values $\alpha_{est}$, the expected surface charge $Q_{est}$ is then calculated at process block 628. The spatial Fourier Transform ($FT_{est}$) of the estimated charge $Q_{est}$ is calculated at process block 630 and this is compared with the measured charge $FT_{meas}$ at process block 632. If the difference ($\delta_L$) is less than a preset threshold as determined at decision block 634, the estimated electrical values ($\alpha_{est}$) for this physical model$_k$ are stored along with the difference value ($\delta_L$) as indicated at process block 636. Otherwise, the system loops back and repeats the process after changing the estimated electrical values ($\alpha_{est}$) by an amount $\delta\alpha$ as indicated by process block 638.

This iterative process is expressed as follows:

$$FT_{meas} - FT_{est} = \frac{\partial FT_t}{\partial \alpha} \cdot \delta\alpha. \tag{10}$$

The difference between $FT_{meas}$ and $FT_{est}$ is used to compute a correction to the electrical property vector, $\delta\alpha$, using the first term in a Taylor's series expansion of the change of $FT_{est}$ given by a numerically calculated matrix of dimensions $N_{Max}$ by $L_{Max}$ written as $$\frac{\partial \overline{FT_{est}}}{\partial \alpha}.$$

Here $N_{max}$ is the number of different regions described in paragraph 0050 and 0051 and $L_{max}$ is the maximum number of Fourier terms. We obtain $\delta\alpha$ by inverting equation (10) with a typically overdetermined set of equations utilizing a Singular Value Decomposition technique.

As determined at decision block 640, all of the $k_{Max}$ variations in the physical model$_k$ are processed in the above-described manner to produce a set of estimated electrical values ($\alpha_{est}$) for each model. The set of stored electrical values ($\alpha_{est}$) which resulted in the smallest difference value ($\delta_L$) is located in the stored values as indicated at process block 642, and this information is used to produce the final image as indicated at process block 644.

An advantage of the present invention over prior techniques which employ separate imaging systems is that the relatively inexpensive optical array may be used to acquire information needed to estimate the physical model$_k$. This system is, therefore, a more desirable breast cancer screening device. However, if the image produced by the present invention reveals a possible malignancy, the acquired surface charge data $Q_j$ may be used in combination with a physical model produced from a high resolution MRI or x-ray CT or ultrasound image to provide a more refined image of the electrical values.

We claim

1. A method for producing an image indicative of an electrical characteristic of an object, the steps comprising:
    a) applying a voltage to a surface of the object with an array of sensor elements that make electrical connection with the surface;
    b) measuring the surface charge at each sensor element that results from the applied voltage;
    c) transforming the surface charge measurements;
    d) estimating the electrical characteristics of the object using information indicative of the surface contour of the object;
    e) calculating, from the transformed surface charge measurements and estimated electrical characteristics of the object, electrical characteristic values throughout the object; and
    f) producing an image of the electrical characteristic of the object from said calculated electrical characteristic values.

2. The method as recited in claim 1 in which step c) is a Fourier transformation.

3. The method as recited in claim 1 in which step d) includes:
    i) measuring the surface contour of the object; and
    ii) producing a physical model of the object using the surface contour measurements.

4. The method as recited in claim 3 in which step d) further includes:
    iii) estimating the presence of anomalies in the object using the transformed surface charge measurements.

5. The method as recited in claim 2 in which step e) includes:
    i) calculating an estimated surface charge pattern produced by the estimated electrical characteristics of the object;
    ii) Fourier transforming the estimated surface charge pattern;
    iii) comparing with the Fourier transformed surface charge pattern with the Fourier transformed surface charge measurements; and
    iv) changing the estimated electrical characteristics of the object and repeating steps i), ii) and iii) until the difference between the Fourier transformed estimated surface charge pattern and the Fourier transformed surface charge measurements is less than a preselected amount.

6. The method as recited in claim 5 in which step d) includes:
    i) measuring the surface contour of the object; and
    ii) producing a plurality of physical models of the object using the surface contour measurements and a corresponding plurality of sets of estimated electrical characteristics.

7. The method as recited in claim 6 in which step e) further includes:
    v) repeating steps i), ii), iii) and iv) with each of said sets of estimated electrical characteristics; and
    vi) selecting the estimated electrical characteristics which result in the least difference between the Fourier transformed estimated surface charge pattern and the Fourier transformed surface charge measurements.

8. The method as recited in claim 1 in which the object is the human breast and step d) includes:
    i) measuring the contour of the breast.

9. The method as recited in claim 8 in which the contour of the breast is measured by establishing an array of light beams, positioning the breast in the array of light beams, and determining which light beams are interrupted by the breast.

* * * * *

UNITED STATES PATENT AND TRADEMARK OFFICE
CERTIFICATE OF CORRECTION

PATENT NO. : 7,627,362 B2  Page 1 of 1
APPLICATION NO. : 10/700876
DATED : December 1, 2009
INVENTOR(S) : Gregory et al.

It is certified that error appears in the above-identified patent and that said Letters Patent is hereby corrected as shown below:

Column 14, claim 5, line 26, "comparing with the" should be --comparing the--.

Signed and Sealed this

Twelfth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,627,362 B2 | Page 1 of 1 |
| APPLICATION NO. | : 10/700876 | |
| DATED | : December 1, 2009 | |
| INVENTOR(S) | : Gregory et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1730 days.

Signed and Sealed this

Second Day of November, 2010

David J. Kappos
*Director of the United States Patent and Trademark Office*